US010646547B2

(12) United States Patent
Kim et al.

(10) Patent No.: US 10,646,547 B2
(45) Date of Patent: May 12, 2020

(54) POLYPEPTIDE HAVING CHEMOKINE ACTIVITY AND USES THEREOF

(71) Applicant: MEDICINAL BIOCONVERGENCE RESEARCH CENTER, Suwon-si, Gyeonggi-do (KR)

(72) Inventors: Sunghoon Kim, Seoul (KR); Min Chul Park, Gyeonggi-do (KR); Byung Woo Han, Seoul (KR); Joon-Sung Park, Seoul (KR)

(73) Assignee: MEDICINAL BIOCONVERGENCE RESEARCH CENTER, Suwon-si, Gyeonggi-do (KR)

( * ) Notice: Subject to any disclaimer, the term of this patent is extended or adjusted under 35 U.S.C. 154(b) by 0 days.

(21) Appl. No.: 15/745,217

(22) PCT Filed: Jul. 13, 2016

(86) PCT No.: PCT/KR2016/007621
§ 371 (c)(1),
(2) Date: Jan. 16, 2018

(87) PCT Pub. No.: WO2017/010807
PCT Pub. Date: Jan. 19, 2017

(65) Prior Publication Data
US 2018/0221448 A1    Aug. 9, 2018

(30) Foreign Application Priority Data

Jul. 14, 2015 (KR) .................. 10-2015-0099994

(51) Int. Cl.
| | |
|---|---|
| A61K 38/16 | (2006.01) |
| A61K 38/19 | (2006.01) |
| C07K 14/52 | (2006.01) |
| C07K 14/00 | (2006.01) |
| G01N 33/574 | (2006.01) |
| G01N 33/58 | (2006.01) |
| G01N 33/50 | (2006.01) |
| G01N 33/68 | (2006.01) |

(52) U.S. Cl.
CPC .............. *A61K 38/19* (2013.01); *C07K 14/52* (2013.01); *G01N 33/50* (2013.01); *G01N 33/574* (2013.01); *G01N 33/58* (2013.01); *G01N 33/6863* (2013.01); *C07K 2319/24* (2013.01); *C07K 2319/50* (2013.01); *G01N 2333/521* (2013.01); *G01N 2800/12* (2013.01); *G01N 2800/7095* (2013.01)

(58) Field of Classification Search
CPC ........ A61K 38/16; A61K 38/19; C07K 14/52; C07K 14/00

USPC ...... 530/300, 324; 514/1.1, 19.3, 21.3, 12.2, 514/18.6, 1.5, 1.6
See application file for complete search history.

(56) References Cited

U.S. PATENT DOCUMENTS

| | | | | |
|---|---|---|---|---|
| 8,986,680 B2 * | 3/2015 | Greene | .................... | C12N 9/93 424/94.5 |
| 2012/0263702 A1 | 10/2012 | Schimmel et al. | | |
| 2013/0209472 A1 * | 8/2013 | Greene | .................... | C12N 9/93 424/139.1 |

FOREIGN PATENT DOCUMENTS

| | | |
|---|---|---|
| JP | 2001-029079 A | 2/2001 |
| WO | WO 2010-107825 A2 | 9/2010 |

OTHER PUBLICATIONS

UniProt K7EJ19, pp. 1-6. Integrated into UniProtKB/TrEMBL Jan. 9, 2013.*
International Preliminary Report on Patentability in corresponding PCT Application No. PCT/KR2016/007621, dated Jan. 16, 2018.
International Search Report and Written Opinion in corresponding PCT Application No. PCT/KR2016/007621, dated Oct. 20, 2016.
NCBI GenBank Accession No. BAG57627.1 (Jul. 31, 2008).
Howard et al., "Histidyl-tRNA Synthetase and Asparaginyl-tRNA Synthetase, Autoantigens in Myositis, Activate Chemokine Receptors on T Lympocytes and Immature Dendritic Cells". The Journal of Experimental Medicine, vol. 196. No. 6, pp. 781-791 (2002).
Stephen F. Altschul, et al., "Basic Local Alignment Search Tool," J. Mol. Biol. (1999) 215, pp. 403-410.
Prabhavathi B. Fernandes, "Technological advances in high-throughput screening," Current Opinion in Chemical Biology, 1998, 2: pp. 597-603.
Stephen F. Altschul, et al., "Gapped BLAST and PSI-BLAST: a new generation of protein database search programs," Nucleic Acids Research, 1997, vol. 25, No. 17, pp. 3389-3402.
Ronald A. Hitzeman, et al., Isolation and Characterization of the Yeast 3-Phosphoglycerokinase Gene (PGK) by an Immunological Screening Technique, The Journal of Biological Chemistry, vol. 255, No. 24, Dec. 1980, pp. 12073-12080.
Lauri Schultz, et al., High Throughput Purification of Combinatorial Libraries, Bioorganic & Medicinal Chemistry Letters 8 (1998) pp. 2409-2414.
G Sitta Sittampalam, et al., "High-throughput screening: advances in assay technologies," Current Opinion in Chemical Biology, 1997, 1: pp. 384-391.
Harold N. Weller, et al., "High throughput analysis and purification in support of automated parallel synthesis," Molecular Diversity 1997, 3: pp. 61-70.

* cited by examiner

*Primary Examiner* — Julie Ha
(74) *Attorney, Agent, or Firm* — Leason Ellis LLP

(57) ABSTRACT

A polypeptide having chemokine activity mediated by binding to C-C chemokine receptor type 3 (CCR3) comprising SEQ ID NO: 1 and uses thereof are described.

Figure 1:
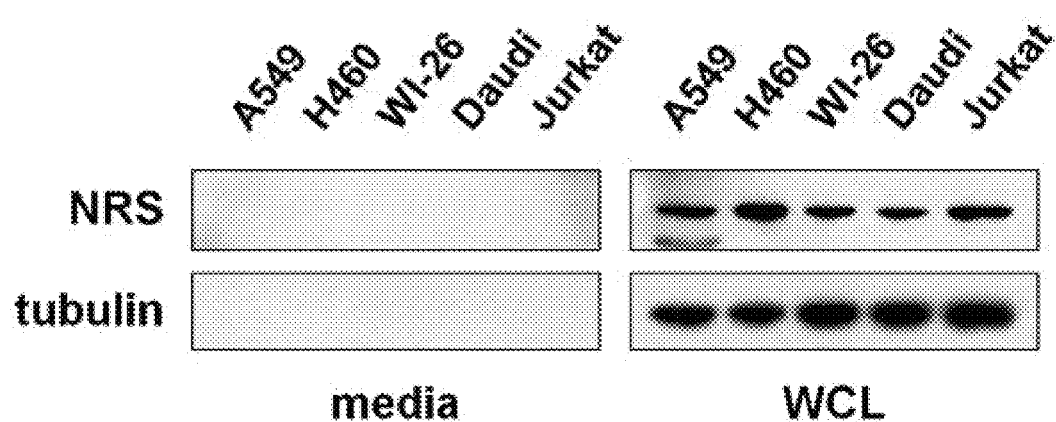

18 Claims, 5 Drawing Sheets
Specification includes a Sequence Listing.

POLYPEPTIDE HAVING CHEMOKINE ACTIVITY AND USES THEREOF

CROSS-REFERENCE TO RELATED PATENT APPLICATIONS

This application is a U.S. National Phase Application under 35 U.S.C. § 371 of International Patent Application No. PCT/KR2016/007621, filed Jul. 13, 2016, and claims priority to KR 10-2015-0099994, filed Jul. 14, 2015, all of which are incorporated by reference in their entireties. The International Application was published on Jan. 19, 2017 as International Publication No. WO 2017/010807 A1.

SEQUENCE LISTING

The instant application contains a Sequence Listing which has been submitted electronically in ASCII format and is hereby incorporated by reference in its entirety. Said ASCII copy, created on Jan. 12, 2018, is named 10524-006504-US0_ST25.txt and is 6.3 bytes in size.

TECHNICAL FIELD

The present invention relates to a novel polypeptide with chemokine activity, and more particularly, to a polypeptide consisting of the amino acid sequence shown in SEQ ID NO: 1 and its use thereof.

BACKGROUND OF THE INVENTION

The present application claims priority to Korean Patent Application No. 10-2015-0099994, filed on Jul. 14, 2015, the entire contents of which are incorporated herein by reference.

Aminoacyl-tRNA synthetase is an enzyme that attaches a specific amino acid precisely to its cognate tRNA and it plays an essential role in protein synthesis. The process of attaching amino acids to respective cognate tRNAs is divided into two stages: The first step is to activate the amino acid to aminoacyl adenylate by consuming one ATP, while the second step is to transfer the activated amino acid to the tRNA. Aminoacyl-tRNA synthetases of mammals have similar roles as those of prokaryotes, but have additional domains. These additional domains have been known to be involved in the formation of various complexes with other aminoacyl-tRNA synthetases or other regulatory factors. It has recently been shown that this structural complexity is related to the functional diversity of aminoacyl-tRNA synthetases and to various human diseases.

Chemokines, on the other hand, play an indispensable role in attracting white blood cells to various tissues of the body as leukocyte chemotactic factors. The process is essential for physical responses to both inflammation and infection. Chemokines and their receptors are central to the pathophysiology of immunomodulatory, inflammatory and infectious diseases. Especially, it has been shown that interaction of specific chemokines with their receptors could elicit certain pathological consequences, including autoimmune diseases. Therapeutic approaches for modulating the activity of chemokines or their receptors have been proposed.

The CC chemokine receptor 3 (CCR3) is a GPCR (G protein-coupled receptor) for chemokines including eotaxin-1, eotaxin-2, RANTES, MCP-2, MCP-3 and MCP-4. CCR3 causes an eosinophilic leukocyte reaction in peripheral blood and airways. CCR3 is expressed not only on the surface of eosinophilic leukocytes but also on that of basophilic leukocytes, mast cells and type 2 helper T lymphocytes. CCR3 mRNA and protein levels are elevated in bronchial mucosa of asthmatic patients in relation to airway hyper-responsiveness. The fact that CCR3 participates in airway infiltration of eosinophilic leukocytes has been demonstrated in CCR3-deficient mice studies. The human CCR3 gene (MIM #601268) is located on chromosome 3p21.3 associated with atopic dermatitis and asthma. Thus, the binding of chemokine ligands to CCR3 is known to be an important regulator of inflammatory and immunomodulatory conditions, including autoimmune diseases such as asthma, rhinitis and allergic diseases and rheumatoid arthritis. Graves' disease and arteriosclerosis, and a variety of pathological contributions of CCR3 have been found, including the ability to detect choroidal neovascularization through a ligand that binds to CCR3, as described in U.S. Pat. No. 8,778,616B2.

In the past, antagonists to a receptor were screened to treat the corresponding receptor-mediated diseases in regard to the ligands and receptors involved in specific pathological phenomena. However, in the case of substantially blocking only the action of the receptor indiscriminately, the adverse effect is caused by the pathologic entry of the lesion into the adaptation state (i.e., other receptors regulate pathology) or excessive suppression of the favorable function of the receptor. The inhibition of the action of the ligand causing the disease on the receptor is also considered to be important in the prevention and treatment of diseases.

DETAILED DESCRIPTION OF THE INVENTION

Technical Problem

Accordingly, the present inventors have completed the present invention after they found that N-terminal extension domain of asparaginyl-tRNA synthetase (NRS) has a chemokine activity, while observing non-translational biological activity of the aminoacyl-tRNA synthetase.

Accordingly, an aspect of the present invention is to provide a polypeptide consisting of the amino acid sequence of SEQ ID NO: 1.

Another aspect of the present invention is to provide a nucleic acid molecule encoding said polypeptide.

Another aspect of the present invention is to provide a recombinant vector comprising the nucleic acid molecule.

Another aspect of the present invention is to provide a transformant transformed with the recombinant vector.

Another aspect of the present invention is to provide a composition for detecting choroidal neovascularization comprising the polypeptide as an active ingredient.

Another aspect of the present invention is to provide a composition for diagnosing CCR3-mediated diseases comprising the polypeptide as an active ingredient.

Still another aspect of the present invention is to provide a composition for drug delivery specific for CCR3-mediated disease comprising the polypeptide as an active ingredient; and a method for screening an agent for preventing or treating CCR3-mediated diseases using the polypeptide.

Still another aspect of the present invention is to provide a use of the polypeptide for preparing an agent comprising the polypeptide as an active ingredient for detecting choroidal neovascularization.

Still another aspect of the present invention is to provide a method for detecting choroidal neovascularization, the method comprising administering an effective amount of an agent for detecting choroidal neovascularization comprising the polypeptide as an active ingredient to a subject in need thereof.

Still another aspect of the present invention is to provide a use of the polypeptide for preparing an agent comprising the polypeptide as an active ingredient for diagnosing CCR3-mediated diseases.

Still further aspect of the present invention is to provide a method for diagnosing CCR3-mediated diseases, the method comprising administering an effective amount of a diagnostic agent for CCR3-mediated diseases comprising the polypeptide as an active ingredient to an individual in need thereof.

Still further aspect of the present invention is to provide a use of the polypeptide for preparing an agent comprising the polypeptide as an active ingredient for a CCR3-mediated disease-specific drug delivery.

Still further aspect of the present invention is to provide a CCR3-mediated disease-specific drug delivery method, the method comprising administering an effective amount of an agent for a CCR3-mediated disease-specific drug delivery comprising the polypeptide as an active ingredient to a subject in need thereof.

Technical Solution

An embodiment according to an aspect of the present invention provides a polypeptide consisting of the amino acid sequence shown in SEQ ID NO: 1.

Another embodiment according to an aspect of the present invention provides a nucleic acid molecule encoding the polypeptide.

Another embodiment according to an aspect of the present invention provides a recombinant vector comprising the nucleic acid molecule.

Another embodiment according to an aspect of the present invention provides a transformant transformed with said recombinant vector.

Another embodiment according to an aspect of the present invention provides a composition for detecting choroidal neovascularization comprising the polypeptide as an active ingredient.

Another embodiment according to an aspect of the present invention provides a composition for diagnosing CCR3-mediated diseases comprising the polypeptide as an active ingredient.

An embodiment according to still another aspect of the present invention provides a composition for drug delivery specific for CCR3-mediated disease comprising the polypeptides as an active ingredient; and a method for screening an agent for preventing or treating CCR3-mediated diseases using the polypeptides.

An embodiment according to still another aspect of the present invention provides a use of the polypeptide for preparing an agent comprising the polypeptide as an active ingredient for detecting choroidal neovascularization.

An embodiment according to still another aspect of the present invention provides a method for detecting choroidal neovascularization, the method comprising administering an effective amount of an agent for detecting choroidal neovascularization comprising the polypeptide as an active ingredient to a subject in need thereof.

An embodiment according to still further aspect of the present invention provides a use of the polypeptide for preparing an agent comprising the polypeptide as an active ingredient for diagnosing CCR3-mediated diseases.

An embodiment according to still further aspect of the present invention provides a method for diagnosing CCR3-mediated diseases, the method comprising administering an effective amount of a diagnostic agent for CCR3-mediated diseases comprising the polypeptide as an active ingredient to an individual in need thereof.

An embodiment according to still further aspect of the present invention provides a use of the polypeptide for preparing an agent comprising the polypeptide as an active ingredient for a CCR3-mediated disease-specific drug delivery.

An embodiment according to still further aspect of the present invention provides a CCR3-mediated disease-specific drug delivery method, the method comprising administering an effective amount of a preparation for a CCR3-mediated disease-specific drug delivery comprising the polypeptide as an active ingredient to a subject in need thereof.

Hereinafter, the present invention will be described in detail.

Definition

Unless defined otherwise, all technical and scientific terms used herein have the same meaning as commonly understood by one of ordinary skill in the art. The following references provide one of the skills with a general definition of the various terms used in the specification of the present invention: Singleton et al., DICTIONARY OF MICROBIOLOGY AND MOLECULAR BIOLOGY (2d ed. 1994); THE CAMBRIDGE DICTIONARY OF SCIENCE AND TECHNOLOGY (Walker ed., 1988); And Hale Marham, THE HARPER COLLINS DICTIONARY OF BIOLOGY. The following definitions are also provided to assist readers in carrying out the present invention.

As used herein, the term "polypeptide" is used interchangeably with "protein" or "peptide" and for example, refers to a polymer of amino acid residues as commonly found in proteins of nature.

The term "polynucleotide" or "nucleic acid" in the present invention refers to deoxyribonucleotides or ribonucleotides in single- or double-stranded form, Unless otherwise constrained, it also includes known analogs of natural nucleotides that hybridize to nucleic acids in a manner similar to naturally occurring nucleotides.

As used herein, the term "expression" refers to the production of a protein or nucleic acid in a cell.

The triplet of amino acids used herein refers to the following amino acids according to standard abbreviations in the biochemistry:

A (Ala): alanine; C (Cys); cysteine; D (Asp): aspartic acid; E (Glu): glutamic acid; F (Phe): phenylalanine; G (Gly): glycine; H (His): histidine; I (Ile): isoleucine; K (Lys): lysine; L (Leu): leucine; M (Met): methionine; N (Asn): asparagine; O (Ply) pyrrolic acid; P (Pro): proline; Q (Gln): Glutamine; R (Arg): arginine; S (Ser): serine; T (Thr): threonine; U (Sec): selenocysteine, V (Val): valine; W (Trp): tryptophan; Y (Tyr): Tyrosine.

The term "NRS" used herein is used interchangeably with 'AsnRS' or 'Asparaginyl-tRNA synthetase (asparagine tRNA synthetase)', and refers to a type of aminoacyl-tRNA synthetase that promotes the attachment of asparagine to its cognate tRNA. In the present invention, unless otherwise stated, the term "NRS" means human NRS, and the human NRS preferably consists of the amino acid sequence shown in SEQ ID NO: 2 below:

```
MVLAELYVSDREGSDATGDGTKEKPFKTGLKALMTVGKEPFPTIYVDSQK

ENERWNVISKSQLKNIKKMWHREQMKSESREKKEAEDSLRREKNLEEAKK

ITIKNDPSLPEPKCVKIGALEGYRGQRVKVFGWVHRLRRQGKNLMFLVLR

DGTGYLQCVLADELCQCYNGVLLSTESSVAVYGMLNLTPKGKQAPGGHEL

SCDFWELIGLAPAGGADNLINEESDVDVQLNNRHMMIRGENMSKILKARS

MVTRCFRDHFFDRGYYEVTPPTLVQTQVEGGATLFKLDYFGEEAFLTQSS

QLYLETCLPALGDVFCIAQSYRAEQSRTRRHLAEYTHVEAECPFLTFDDL

LNRLEDLVCDVVDRILKSPAGSIVHELNPNFQPPKRPFKRMNYSDAIVWL

KEHDVKKEDGTFYEFGEDIPEAPERLMTDTINEPILLCRFPVEIKSFYMQ

RCPEDSRLTESVDVLMPNVGEIVGGSMRIFDSEEILAGYKREGIDPTPYY

WYTDQRKYGTCPHGGYGLGLERFLTWILNRYHIRDVCLYPRFVQRCTP
```

An Aspect of the Present Invention Provides a Polypeptide Consisting of the Amino Acid Sequence Shown in SEQ ID NO: 1.

The polypeptide of the present invention is derived from human NRS and may be referred to herein interchangeably with NRS fragment, NRS N-term fragment, and the like. The polypeptide of the present invention is composed of a sequence located in the N-terminal extension domain of human NRS, and preferably consists of the amino acid sequence of SEQ ID NO: 1.

The NRS fragment of SEQ ID NO: 1 of the present invention is characterized in that it has chemokine activity. The chemokine activity is mediated by the NRS fragment of SEQ ID NO: 1 of the present invention binding to CCR3 (C-C chemokine receptor type 3). This is well illustrated in following Examples of the present invention. The amino acid sequence of SEQ ID NO: 1 is as follows:

```
MVLAELYVSDREGSDATGDGTKEKPFKTGLKALMTVGKEPFPTIYVDSQK

ENERWNVISKSQLKNIKKMWHREQMKS
```

The polypeptides according to the present invention can be extracted from nature or can be constructed by genetic engineering methods. For example, a nucleic acid encoding the polypeptide or a functional equivalent thereof (e.g., SEQ ID NO: 3) is constructed according to a conventional method. The nucleic acid can be constructed by FOR amplification using an appropriate primer. Alternatively, DNA sequences may be synthesized by standard methods known in the art, for example, using an automated DNA synthesizer (commercially available from Biosearch or Applied Biosystems). The constructed nucleic acid is inserted into a vector containing one or more expression control sequences (e.g., promoters, enhancers, etc.) operatively linked to the expression of the nucleic acid, and a host cell is transformed with the recombinant expression vector formed therefrom. The resulting transformant is cultured under a medium and conditions suitable for the expression of the nucleic acid. And then the pure polypeptide encoded by the nucleic acid sequence was substantially recovered from the culture. The recovery of the polypeptide can be carried out using methods known in the art (for example, chromatography). As used herein, "substantially pure polypeptide" means that the polypeptide according to the invention is substantially free of any other proteins derived from the host cell. Genetic engineering methods for the synthesis of polypeptides of the present invention can be found in the following references: Maniatis et al., Molecular Cloning; A laboratory Manual, Cold Spring Harbor laboratory, 1982; Sambrook et al., Molecular Cloning: A Laboratory Manual, Cold Spring Harbor Press, N.Y., Second (1998) and Third (2000) Editions; Gene Expression Technology, Method in Enzymology, Genetics and Molecular Biology, Method in Enzymology, Guthrie Fink (eds.), Academic Press, San Diego, Calif., 1991; And Hitzeman et al., J. Biol. Chem., 255:12073-12080, 1990.

In addition, the polypeptides of the present invention can be readily prepared by chemical synthesis known in the art (Creighton, Proteins, Structures and Molecular Principles, W. H. Freeman and Co., NY, 1983). Representative methods include, but are not limited to, liquid or solid phase synthesis, fractional condensation, F-MOC, or T-BOC chemistry (Chemical Approaches to the Synthesis of Peptides and Proteins, Williams et al., Eds., CRC Press, Boca Raton Fla., 1997; A Practical Approach, Atherton Sheppard, Eds., IRL Press, Oxford, England, 1989).

In addition, the polypeptide of the present invention includes not only polypeptides having the amino acid sequences described above, but also amino acid sequence variants thereof within the scope of the present invention. A variant of the polypeptide of the present invention refers to a polypeptide in which at least one amino acid residue in the amino acid sequence of the present invention has a different sequence by deletion, insertion, non-conservative or conservative substitution, substitution of amino acid analog, or a combination thereof. Amino acid exchanges that do not overall after the activity of the molecule are known in the art (H. Neurath, R. L. Hill, The Proteins, Academic Press, New York, 1979).

In some cases, the polypeptide of the present invention may be modified by phosphorylation, sulfation, acrylation, glycosylation, methylation, and farnesylation.

In addition, polypeptides comprising an amino acid sequence of SEQ ID NO: 1 or an amino acid sequence having at least 95% sequence homology thereto, and comprising 77 to 100 amino acids are also included in the scope of the present invention.

The present invention also provides a polypeptide further comprising two amino acids at the N-terminus of the polypeptide of SEC) ID NO: 1, Preferably, the two amino acids may be, but are not limited to, glycine and histidine.

The polypeptide of the present invention includes functional equivalents of the polypeptide represented by SEQ ID NO: 1. The term "functional equivalent" refers to a polypeptide having at least 70%, preferably at least 80%, more preferably at least 90% sequence homology (or identity) with the amino acid sequence of the polypeptide of the present invention. For example, the polypeptide of the present invention, which includes a polypeptide having 70%, 71%, 72%, 73%, 74%, 75%, 76%, 77%, 78%, 79%, 800%, 810%, 820%, 830%, 840%, 850%, 860%, 870%, 880%, 890%, 900%, 910%, 920%, 93%, 94%, 95%, 96%, 97%, 98%, 99%, and 100% sequence homology, refers to a polypeptide exhibiting substantially the same physiological activity as the polypeptide of the present invention. Here, the term "substantially" means a state that indicates a property of a certain property to a total or almost the same degree.

In the present invention, "homology or identity" means the overall association between polymer molecules, such as polypeptide molecules. For example, calculation of homology/identity (%) between two polypeptide sequences can be performed by aligning two sequences for optimal comparison. Preferably, the length of the sequence arranged for comparison is at least 30%, at least 40%, at least 50%, at least 60%, at least 70%, at least 80% %, at least 90%, or substantially 100%. Then, the amino acids at the corresponding amino acid sites are compared with each other. When the amino acid located at the site of the first sequence is identical to the amino acid at the corresponding site of the second sequence, the two sequences are identical at that site. The identity (%) of two sequences is a function of the number of sites having amino acids that are common in two sequences, while considering the number and length of gaps that must be introduced for optimal alignment between the two sequences. The comparison between two sequences and the determination of identity (%) can be performed through a mathematical algorithm. For example, ClustalW (Thompson et al., 1994) can be used to measure sequence identity values using the following parameters: Pair Array Parameters—Method: Accurate, Matrix: PAM, Gap open penalty: 10.00, Gap extension penalty: 0.10; Multiple array parameters—Matrix: PAM, Gap open penalty: 10.00, delay equality (%): 30, penalize end gaps: on, Gap separation distance: 0, Negative Matrix: no, gap extension penalty: 0.20, residue-specific gap penalties: on, hydrophilic gap penalty: on, hydrophilic residue: GPSNDQEKR. Sequence identity in a particular residue simply includes the same residue derivatized.

The term "substantially" in the present invention means a state indicating the same or nearly the same property of a certain property. The term "substantially the same" in the present invention is used in connection with comparison between amino acids or nucleic acid sequences. Those of ordinary skill hi the art will understand that two sequences are "substantially identical" if they have the same residue at the corresponding site. As is well known in the art, amino acid or nucleic acid sequences can be compared using a wide variety of algorithms. For example, BLASTN for nucleic acid sequence comparisons, BLASTP for amino acid sequence comparison, gapped BLAST, and PSI-BLAST can be used as computer programs. Examples of such computer programs are described in the following references: Altschul et al., Basic local alignment search tool, *J. Mol. Biol.*, 215(3): 403-410, 1990; Altschul et al., Methods in Enzymology, Altschul et al., *Nucleic Acids Res.* 25:3389-3402, 1997; Baxevanis et al., *Bioinformatics: A Practical Guide to the Analysis of Genes and Proteins*, Wiley, 1998; And Misener et al., (eds.), *Bioinformatics Methods and Protocols* (Methods in Molecular Biology, Vol. 132), Humana Press, 1999. In addition to searching for identical sequences, the computer programs described above typically provide a degree of identity. The two sequences, when at least 70%, preferably at least 80%, at least 85%, at least 90%, at least 91%, at least 92%, at least 93%, at least 94%, at least 95%, at least 96%, at least 97%, at least 98%, and at least 99% of the residues in the corresponding site over a certain length of residue are identical, are considered to be "substantially identical". Preferably, the "constant length residues" refer to residues of at least 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500, or more residues.

The term "corresponding" as used herein is often used to determine the position/identity of the amino acid residues of given polypeptides. As a conventional technician, residues in polypeptides are often designated using a canonical numbering system based on reference-related polypeptide.

The "functional equivalents" may be those in which some of the amino acid sequences of the polypeptides of the invention are produced as a result of addition, substitution or deletion. The substitution of the amino acid is preferably a conservative substitution. Examples of conservative substitutions of amino acids present in nature include: aliphatic amino acids (Gly, Ala, Pro), hydrophobic amino acids (Ile, Leu, Val), aromatic amino acids (Phe, Tyr, Trp), acidic amino acids (Asp, Glu), basic amino acids (His, Lys, Arg, Gln, Asn) and sulfur-containing amino acids (Cys, Met), In addition, the functional equivalents also include variants in which a portion of the amino acid is deleted in the amino acid sequence of the polypeptide of the invention. The deletion or substitution of the amino acid is preferably located in a region that is not directly related to the physiological activity of the polypeptide of the present invention. In addition, deletion of the amino acid is preferably located in a portion not directly involved in the physiological activity of the polypeptide of the present invention. In addition, the polypeptide of the present invention includes variants in which several amino acids are added at both ends of the amino acid sequences or within the amino acid sequences. The scope of the functional equivalents of the present invention also comprises proteins or polypeptide derivatives in which some of the chemical structures of proteins are modified while maintaining the basic skeleton of the protein according to the present invention and its physiological activity. This includes, for example, structural modifications to alter the stability, shelf stability, volatility, or solubility of the protein of the present invention.

The present invention also provides a nucleic acid molecule encoding the polypeptide of the present invention.

As described above, as long as the nucleic acid sequence encoding the polypeptide of the present invention encodes a polypeptide having equivalent activity, one or more nucleic acid bases may be mutated by substitution, deletion, insertion, or a combination thereof. The polypeptide of SEQ ID NO: 1 of the present invention described above is preferably encoded by a nucleic acid molecule represented by the nucleotide sequence of SEQ ID NO: 3. The sequence of such a nucleic acid molecule may be single- or double-stranded, and may be a DNA molecule or RNA (mRNA) molecule. The nucleotide sequence of SEQ ID NO: 3 is as follows:

```
ATGGTGCTTGCAGAGCTGTACGTCTCTGACCGAGAGGGAAGCGATGCCAC

GGGAGATGGAACCAAGGAGAAACCATTTAAAACAGGTCTAAAGGCTTTGA

TGACAGTAGGGAAAGAACCATTTCCTACCATTTACGTAGATTCACAAAAA

GAAAATGAGAGGTGGAATGTTATTTCTAAATCACAGTTGAAGAACATTAA

AAAGATGTGGCATAGGGAACAAATGAAGAGT
```

The nucleic acid sequence encoding the polypeptide of the present invention can be isolated from nature, artificially synthesized or produced by genetic recombination methods. The nucleic acid sequence encoding the polypeptide of the present invention may be operably linked to a vector capable of expressing it to provide the polypeptide of the present invention.

The polypeptides of the present invention can be constructed by conventional genetic engineering methods. The polynucleotide sequence can be constructed, for example, by FOR amplification using an appropriate primer having a polynucleotide encoding the human NRS gene as a template. Alternatively, DNA sequences can be synthesized by standard methods known in the art, for example, using an automated DNA synthesizer (commercially available from Biosearch or Applied Biosystems). The constructed polynucleotide sequence may be operatively linked to one or more expression control sequences (e.g., promoters, enhancers, etc.) that regulate expression of the polynucleotide sequences. And then the host cells are transformed with a recombinant expression vector constructed therefrom. The resulting transformant is cultured under media and conditions suitable for the expression of the DNA sequence to recover substantially pure protein encoded by the DNA sequence from the culture. The recovery may be carried out using methods known in the art.

As used herein, "substantially pure polypeptide or protein" means that the protein according to the invention is substantially free of any other proteins derived from the host cell. Genetic engineering methods for the protein synthesis of the present invention can be found in the following references: Maniatis et al., Molecular Cloning; A laboratory Manual, Cold Spring Harbor laboratory, 1982; Sambrook et al., supra; Gene Expression Technology, Method in Enzymology, Genetics and Molecular Biology, Method in Enzymology, Guthrie & Fink (eds.), Academic Press, San Diego, Calif., 1991; And Hitzeman et al., J. Biol. Chem., 255: 12073-12080, 1990.

In addition, the polypeptide of the present invention can be chemically synthesized by a technique known in the art (Creighton, Proteins: Structures and Molecular Principles, W.H. Freeman and Co., NY, 1983). In other words, the polypeptides of the present invention can be prepared using a conventional stepwise liquid or solid phase synthesis, fractional condensation, F-MOC or T-BOC chemistry (Chemical Approaches to the Synthesis of Peptides and Proteins, Williams et al., Eds., CRC Press, Boca Raton Fla., (1997); A Practical Approach, Atherton Sheppard, Eds., IRL Press, Oxford, England, (1989)). A preferred method of preparation is to use solid phase synthesis. The polypeptide of the present invention can be synthesized by proceeding sequentially in accordance with the amino acid sequence identified starting from the C-terminus in the conventional solid phase method by a condensation reaction between protected amino acids. After the condensation reaction, the protecting group and the carrier to which the C-terminal amino acid is linked can be removed by a known method such as acid decomposition or aminolysis. The above-mentioned peptide synthesis methods are described in detail in related books (Gross and Meienhofer's, The Peptides, vol 2., Academic Press, 1980).

The protein produced by the genetic engineering method or the chemically synthesized protein can be separated and purified by various methods such as extraction, recrystallization, various chromatography (gel filtration, ion exchange, precipitation, adsorption, reversed phase), electrophoresis, and countercurrent distribution method known in the art.

The Present Invention Provides a Recombinant Vector Comprising the Nucleic Acid Molecule.

The term "recombinant vector" in the present invention refers to a gene construct comprising an essential regulatory element operatively linked to express an inserted gene, as a vector capable of expressing a target protein or a target RNA in a suitable host cell.

The term "operably linked" in the present invention refers to a functional linkage between a control sequence of a nucleic acid expression and a nucleic acid sequence encoding a desired protein or RNA to perform a general function. For example, a nucleic acid sequence encoding a promoter and a protein or RNA is operably linked so that they can affect the expression of the coding nucleic acid sequence. The operative linkage with the recombinant vector can be produced using genetic recombination techniques well known in the art, and site-specific DNA cleavage and linkage are made using enzymes generally known in the art.

The vector of the present invention includes, but is not limited to, a plasmid vector, a cosmid vector, a bacteriophage vector, and a viral vector. Suitable expression vectors include expression control elements such as promoters, operator, initiation codon, termination codon, polyadenylation signal and enhancer. In addition, they comprise a signal sequence or leader sequence for membrane targeting or secretion and may be prepared variously according to the purpose. The promoter of the vector may be constitutive or inducible. The expression vector also includes a selection marker for selecting a host cell containing the vector, while if the expression vector is a replicable vector, it has a replication origin.

While being not limited thereto, the signal sequence includes a PhoA signal sequence, an OmpA signal sequence and the like when the host is *Escherichia* sp.; an α-amylase signal sequence, a subtilisin signal sequence and the like when the host is *Bacillus* sp.; an MF signal sequence, a SUC2 signal sequence and the like when the host is yeast; an insulin signal sequence, an alpha-interferon signal sequence, an antibody molecule signal sequence and the like when the host is an animal cell.

The Present Invention Provides a Transformant Transformed with the Recombinant Vector.

The transformation includes any method of introducing a nucleic acid into an organism, cell, tissue or organ, and can be carried out by selecting a suitable standard technique depending on a host cell as known in the art. Such methods include microprojectile bombardment, electroporation, protoplast fusion, calcium phosphate ($CaPO_4$) precipitation, calcium chloride ($CaCl_2$) precipitation, agitation with silicon carbide fibers, agrobacterium-mediated transformation, PEG-mediated fusion, microinjection, liposome-mediated method, dextran sulfate, lipofectamine, and thermal shock method, but are not limited thereto.

The term 'transformant' may be used interchangeably with 'host cell' and means a prokaryotic or eukaryotic cell which contains heterologous DNA introduced into the cell by any methods (e.g., electroporation, calcium phosphatase precipitation, microinjection, transformation, and virus infection).

Since the expression level and modification of a protein are different depending on the host cell, the host cell suitable for the purpose of the person skilled in the art can be selected and used. The transformant of the present invention may preferably indicate a transformed microorganism. Specifically, for example, the host cells include, but are not limited to, *Escherichia coli*, *Bacillus subtilis*, *Streptomyces*, *Pseudomonas*, *Proteus mirabilis*, or *Staphylococcus* such as prokaryotic host cells. In addition, cells which are derived from sub-eukaryotic cells including fungi (for example, *Aspergillus*), and yeast (for example, *Pichia pastoris*, *Saccharomyces cerevisiae*, *Schizosaccharomyces*, and *Neurospora crassa*), and higher eukaryotes including insect cells, plant cells, and mammals can be used as the host cells, but the present invention is not limited thereto.

The transformant (or the transformed microorganism) of the present invention can be preferably *Escherichia coli*. The *Escherichia coli* strain of the present invention can be used, for example, Rosetta2 (DE3), 041 (DE3), and SoluBL21, but is not limited to.

Meanwhile, the polypeptide of the present invention (NRS fragment of SEQ ID NO: 1) binds specifically to CCR3, and thus can be used for the purpose of detecting and diagnosing a disease or pathology in which CCR3 is specifically expressed. Specifically, blindness in AMD (aging-associated macular degeneration) mostly results from retinal invasion by choroidal neovascularization, while CCR3 is specifically expressed in the choroidal neovascular endothelial cells of AMD patients. Accordingly, the present invention provides a composition for detecting choroidal neovascularization comprising the polypeptide of the present invention as an active ingredient. Particularly, in the subclinical choroidal neovascularization (CNV), the polypeptide of the present invention can provide convenience for its detection and diagnosis.

The polypeptide of the present invention may be provided in a labeled state to facilitate confirmation, detection and quantification of cell binding (i.e., cell binding to CCR3) to the choroidal neovascularization site of the polypeptide of the present invention. In other words, they may be provided by linking (e.g., covalent bond or crosslink) to a detectable label. The detectable label may be including a chromogenic enzyme (e.g., peroxidase, alkaline phosphatase), a radioactive isotope (e.g., $^{18}F$, $^{123}I$, $^{124}I$, $^{125}I$, $^{32}P$, $^{35}S$, and $^{67}Ga$), chromophore, luminescent substance or fluorescent substance (e.g., FITC, RITC, and GFP (Green Fluorescent Protein); EGFP (Enhanced Green Fluorescent Protein), RFP (Red Fluorescent Protein); DsRed (*Discosoma* sp. Red fluorescent protein); CFP (Cyan Fluorescent Protein), CGFP (Cyan Green Fluorescent Protein), YFP (Yellow Fluorescent Protein), Cy3, Cy5 and Cy7.5), magnetic resonance imaging materials (e.g., Gadolinium (Gd)), superparamagnetic particles, or ultrasuper paramagnetic particles.

The detection method according to the label is widely known in the art, but can be performed, for example, by the following method. When a fluorescent substance is used as a detectable label, immunofluorescence staining can be used. For example, the peptide of the present invention labeled with a fluorescent substance can be reacted with a sample, and unbound or non-specific binding products can be removed. And then fluorescence by the peptide can be observed under a fluorescence microscope. In the case of using an enzyme as a detectable label, the absorbance can be measured by a color reaction of the substrate through an enzyme reaction, and in the case of a radioactive substance, the amount of emitted radiation can be measured. In addition, the detected result may be imaged according to a known imaging method according to the detection label.

In the present invention, the term "sample" refers to a biological sample including blood and other liquid samples of biologic origin, biopsy specimens, solid tissue samples such as tissue culture, or cells derived therefrom. The sample can be obtained from an animal, preferably a mammal. The sample may be pre-treated prior to use for detection. Such a pre-treatment of the sample may include, for example, extraction, concentration, inactivation of interfering components, and addition of reagents.

Since the polypeptide of the present invention has an excellent effect of specifically binding to CCR3, it can be used for diagnosis of CCR3-mediated diseases, or as an intelligent drug delivery vehicle for selectively delivering a drug to a lesion in a CCR3-mediated disease. Accordingly, the present invention provides a composition for diagnosing a CCR3-mediated disease comprising the polypeptide as an active ingredient; and a composition of a CCR3-mediated disease-specific drug delivery comprising the polypeptide as an active ingredient.

In the present invention, the CCR3-mediated disease is a pathological phenomenon in which the expression of CCR3 is specifically expressed in the disease and the activity is increased as compared with a normal state. Therefore, it refers to a disease that can be treated by CCR3 receptor antagonist since the CCR3 acts as a major disease mechanism of the disease. The CCR3-mediated disease includes, but is not limited to, asthma, allergic rhinitis, hypersensitive lung disease, hypersensitivity pneumonia, eosinophilic pneumonia, respiratory allergic diseases, inflammatory bowel disease, psoriasis, dermatitis, eczema, inflammatory skin diseases, kidney cancer, and prostate cancer.

On the other hand, the fact that the polypeptide of the present invention specifically binds to CCR3 to exhibit chemokine activity suggests that human NRS binds to CCR3 at a position (i.e., N-terminal extension site) that includes the polypeptide of the present invention to induce an excessive immune response (including autoimmune response) and CCR3-mediated disease.

Inhibiting the expression of NRS or its function in order to inhibit the action of NRS on the disease affects the innate function of human NRS which plays an essential role in the process of protein translation, and also may cause other side effects. Therefore, among NRS, to find substances acting only at sites related to the immune response and disease and inhibiting their activity locally can reduce the side effects and obtain the desired effect. Thus, to find substances with high selectivity and specificity is considered to be meaningful in the treatment of disease. And thus this is different from simply looking for an antagonist for a specific receptor.

Thus, the use of the polypeptide of the present invention has the advantage of screening for a more specific and highly effective therapeutic agent for inhibiting the activity of a disease-affecting site in NRS.

Therefore, the present invention provides a method for screening an agent for preventing or treating a CCR3-mediated disease, the method comprising (a) determining whether a test agent inhibits the chemokine activity of the polypeptide of SEQ ID NO: 1 or a full-length NRS containing the same, by contacting the test agent with the polypeptide of the present invention (NRS fragment of SEQ ID NO: 1);

(b) selecting a test agent inhibiting chemokine activity in step (a); and (c) determining whether or not CCR3 activity is inhibited by treating the test agent selected in step (b) on cells expressing CCR3.

As used herein, the term "agent" or "test agent" includes any substance, molecule, element, compound, entity or a combination thereof. For example, it includes, but is not limited to, proteins, polypeptides, small organic molecules, polysaccharides, and polynucleotides. It can also be a natural product, a synthetic compound, chemical compound, or a combination of two or more substances. Unless otherwise specified, the agents, materials, and compounds may be used interchangeably.

More specifically, the test agent that can be screened by the screening method of the present invention includes polypeptides, beta-turn mimetics, polysaccharides, phospholipids, hormones, prostaglandins, steroids, aromatic compounds, heterocyclic compounds, benzodiazepines, oligomeric N-substituted glycines, oligocarbamates, saccharides, fatty acids, purines, pyrimidines, their derivatives, structural analogs, or combinations thereof. Some test agents may be synthetic, while other test agents may be natural. The test agent can be obtained from a wide variety of sources including libraries of synthetic or natural compounds. A combinatorial library can be produced with a variety of compounds that can be synthesized step-by-step. Compounds of multiple combinatorial libraries can be produced by encoded synthetic libraries (ESL) methods (WO 95/12608, WO 93/06121, WO 94/08051, WO 95/395503 and WO 95/30642). Peptide libraries can be prepared by the phage display method (WO91/18980). Libraries of natural compounds in the form of bacterial, fungal, plant and animal extracts can be obtained from commercial sources or collected in the field. Known pharmacological agents can be applied to direct or random chemical modifications such as acylation, alkylation, esterification, and amidification to produce structural analogs.

The test agent may be a naturally occurring protein or a fragment thereof. Such test agents can be obtained from natural sources, such as cell or tissue lysates. Libraries of polypeptide preparations can be obtained, for example, by conventional methods or from commercially available cDNA libraries. The test agent may be a peptide. For example, the peptide has about 5-30 amino acids, preferably about 5-20 amino acids, and more preferably about 7-15 amino acids. The peptide may be a naturally occurring protein, a random peptide or a cleavage of a "biased" random peptide.

The test agent may also be "nucleic acid. The nucleic acid test agent may be a naturally occurring nucleic acid, a random nucleic acid, or a "biased" random nucleic acid. For example, fragments of prokaryotic or eukaryotic genomes can be used in a similar manner to those described above.

The test agent may also be a small molecule (e.g., a molecule having a molecular weight of about 1,000 or less). A high throughput assay can be preferably applied to the method for screening the small molecule control agent. Many assays are useful for screening (Shultz, Bioorg. Med. Chem. Lett., 8:2409-2414, 1998; Weller, Mol. Drivers., 3:61-70, 1997; Fernandes, Curr. Opin. Chem. Biol., 2:597-603, 1998; and Sittampalam, Curr. Opin. Chem. Biol., 1:384-91, 1997).

Libraries of test agents screened in the methods of the present invention can be prepared based on structural studies of the polypeptides or analogs of the present invention. This structural study allows the identification of test agents that are capable of inhibiting only negative disease-related activities, while the test agent binds to the chemokine active region of NRS and maintains the innate function associated with protein production. The three dimensional structure of the polypeptides of the present invention can be studied in a number of ways, such as crystal structure and molecular modeling. Methods for studying protein structures using X-ray crystallography are well known in the literatures: Physical Bio-Chemistry, Van Holde, K. E. (Prentice-Hall, New Jersey 1971), pp. 221-239, and Physical Chemistry with Applications to the Life Sciences, D. Eisenberg, D. Crothers (Benjamin Cummings, Menlo Park 1979). Computer modeling of the polypeptide structures of the present invention provides other methods for the design of test agents for screening. Molecular modeling methods are described in the literatures: U.S. Pat. No. 612,894 and U.S. Pat. No. 5,583,973. In addition, the protein structure can also be determined by neutron diffraction and nuclear magnetic resonance (NMR): Physical Chemistry, 4th Ed. Moore, W. J. (Prentice-Hall, New Jersey 1972) and NMR of Proteins and Nucleic Acids, K. Wuthrich (Wiley-Interscience, New York 1986).

The method for determining whether or not to suppress the chemokine activity in the step (a) may be performed according to a method known in the art. Non-limiting examples of this include agar-plate method (Curr Microbiol 30 (4): 2513), Boyden chamber assay method (J Exp Med 115 (3): 45366), Bridge chamber assay method (J. of Cell Biology 75 (2): 606616), microtubule assay method (Anal Biochem 135 2): 4669, Acta Protozoal 34: 1815.) and T-maze assay method (J Protozool 29 (2): 22630)

The CCR3-expressing cells in step (c) include, but are not limited to, eosinophils, basophils, mast cells, and helper T lymphocytes.

In addition, after the step of (C), step (d) may be further carried out in which the selected agent is administered to an animal having a CCR3-mediated disease to test whether it exhibits a therapeutic effect.

The present invention provides a use of the polypeptide for preparing an agent comprising the polypeptide as an active ingredient for detecting choroidal neovascularization.

The present invention provides a method for detecting choroidal neovascularization, the method comprising administering an effective amount of an agent for detecting choroidal neovascularization comprising the polypeptide as an active ingredient to a subject in need thereof.

The present invention provides a use of the peptide for preparing an agent comprising the polypeptide as an active ingredient for diagnosing CCR3-mediated diseases.

The present invention provides a method for diagnosing CCR3-mediated diseases, the method comprising administering an effective amount of a diagnostic agent for CCR3-mediated diseases comprising the polypeptide as an active ingredient to a subject in need thereof.

The present invention provides a use of the polypeptide for preparing a CCR3-mediated disease-specific drug delivery agent comprising the polypeptide as an active ingredient.

The present invention provides a CCR3-mediated disease-specific drug delivery method, the method comprising administering an effective amount of a CCR3-mediated disease-specific drug delivery agent comprising the polypeptide as an active ingredient to a subject in need thereof.

As used herein, the effective amount refers to an amount of detecting, diagnosing or treating choroidal neovascularization or CCR3-mediated disease when administered to a subject. The subject may be an animal, preferably a mammal, particularly an animal including a human, and may be cells, tissues, and organs derived from an animal. The subject may be a patient requiring treatment.

As used herein, the treatment broadly refers to ameliorating symptoms due to choroidal neovascularization or CCR3-mediated disease, which may include treating, substantially preventing, or ameliorating the condition of choroidal angiogenesis or CCR3-mediated disease, and includes, but is not limited to, relieving, curing or preventing one or most of the symptoms resulting from choroidal neovascularization or CCR3-mediated disease.

Effects of the Invention

Since the polypeptide of the present invention is composed of SEQ ID NO: 1 and exhibits chemokine activity through binding to CCR3, it is effective for various purposes such as immuno-regulation, the detection, diagnosis, treatment and development of medicines for CCR3-mediated diseases or pathologies.

BRIEF DESCRIPTION OF THE DRAWINGS

FIG. 1 shows the results of confirming the secretion of NRS by Western blotting after culturing A549, H460, WI-26, Daudi, and Jurkat cell lines for 6 hours in serum-free media, collecting the culture medium, and precipitating the secreted proteins by TCA treatment.

FIG. 2 shows the results of confirming the secretion of NRS by Western blotting after culturing RAW264.7, J774A.1, U937 and HL-60 cell lines in serum-free media for 6 hours, collecting the culture medium, and precipitating the secreted proteins by TCA treatment.

Figure 3:
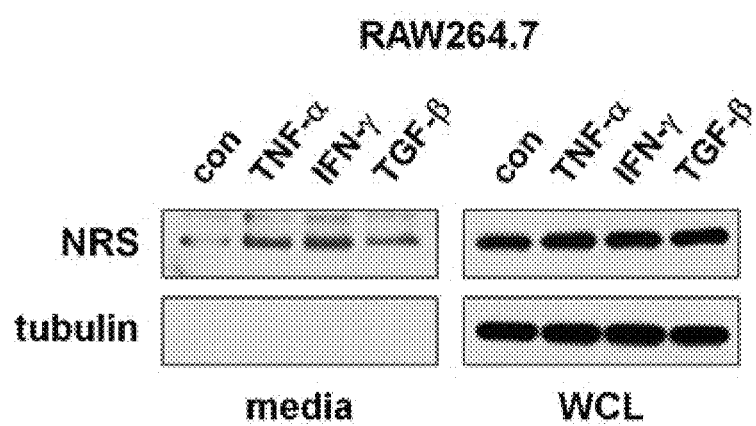

FIG. 3 shows the result of confirming the secretion level of NRS when RAW 264.7 cells were treated with cytokines (TNF-α, IFN-γ and TGH-β) at a concentration of 10 ng ml for 4 hours, respectively (Con: untreated cytokine group).

Figure 4:
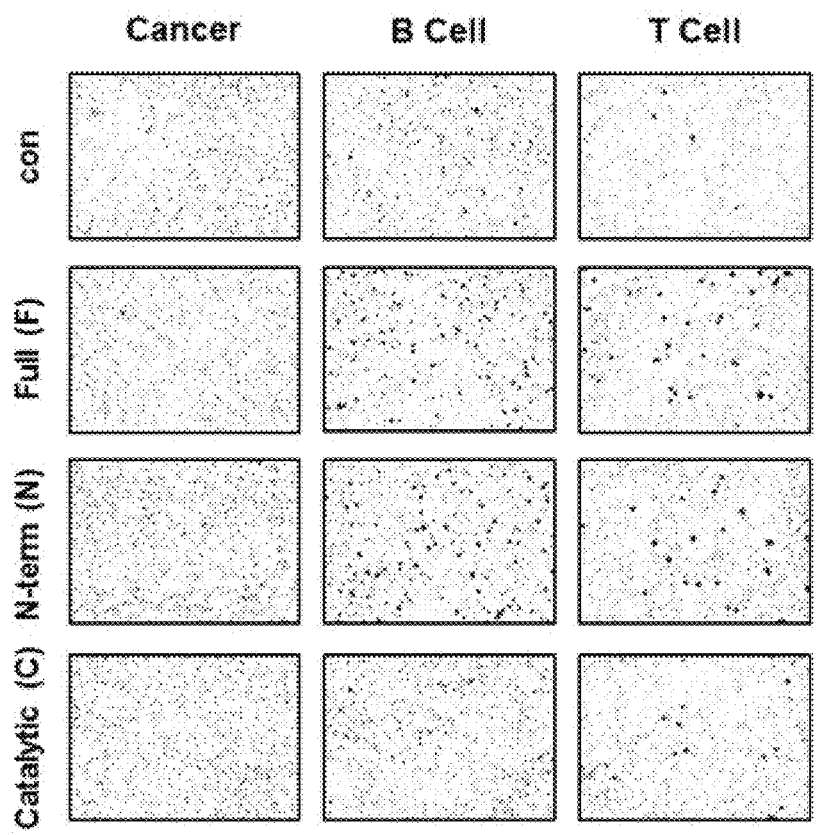

FIG. 4 shows the results of confirming whether cell migration of cancer cells or lymphocytes (T cells, B cells) was induced by the full length NRS, the NRS N-term fragment of the present invention and the NRS catalytic domain peptide, respectively. The tumor cells and lymphocyte cells were spread in an upper chamber having a membrane coated with transwell fibronectin, and the above three kinds of peptides were treated in a lower chamber at a concentration of 1 nM. After incubation for 4 hours, the cells transferred to the membrane were stained and observed under a microscope (T lymphocyte: Jurkat, B lymphocyte: Daudi, Cancer cell: H460).

Figure 5:
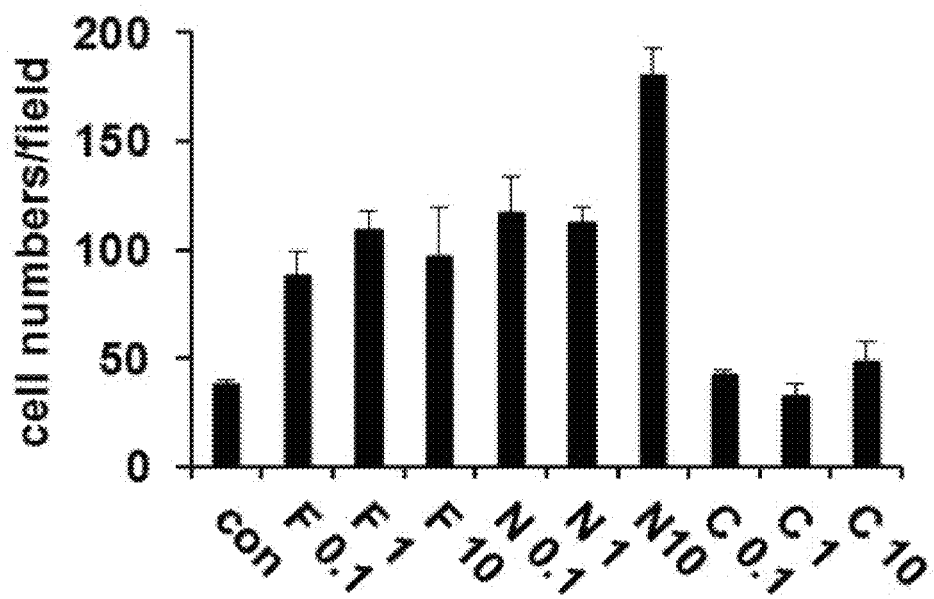

FIG. 5 shows the results of quantifying the cell migration of B lymphocytes (Daudi cells) according to the treatment concentration of each peptide, i.e., the full length NRS, the NRS N-term fragment of the present invention, and the NRS catalytic domain peptide, respectively. After the cell migration assay using transwell for each treatment group, the mobile cells present in the membrane were counted. (con: untreated group, F0.1: full length NRS 0.1 nM treatment, F1: full length NRS 1 nM treatment, F10: full length NRS 10 nM treatment, NO. 1: NRS N-term fragment 0.1 nM treatment, N1: the NRS N-terminal fragment 1 nM treatment, N10: the NRS N-terminal fragment 10 nM treatment, 00.1: the NRS catalytic domain peptide 0.1 nM treatment, C1 the NRS catalytic domain peptide 1 nM treatment, and C10: NRS catalytic domain peptide 10 nM treatment).

Figure 6:
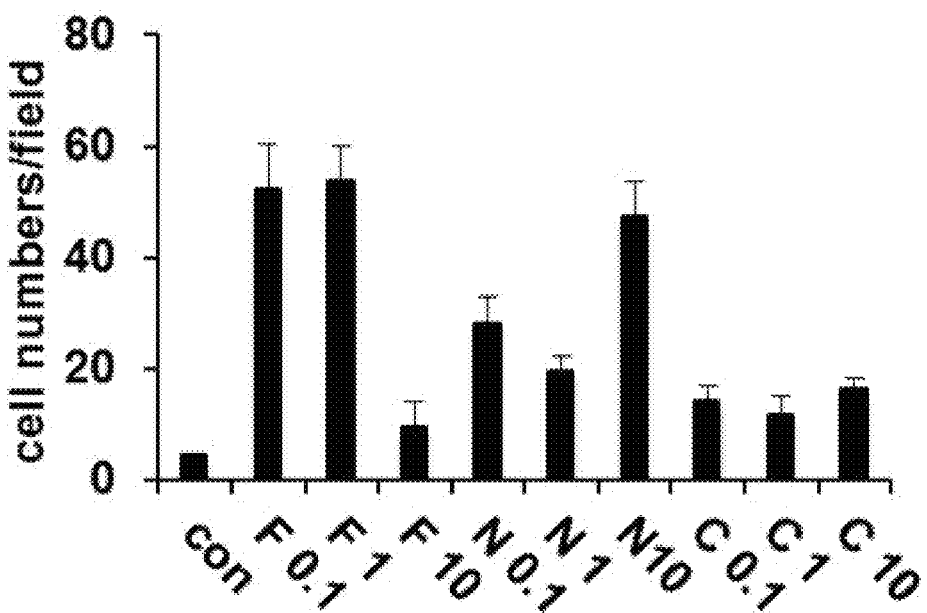

FIG. 6 shows the results of quantifying cell migration of T lymphocytes (Jurkat cell) according to the treatment concentration of each peptide, i.e., the full length NRS, the NRS N-term fragment of the present invention, and the NRS catalytic domain peptide, respectively. After the cell migration assay using transwell for each treatment group, the mobile cells present in the membrane were counted. (con: untreated group, F0.1: full length NRS 0.1 nM treatment, F1: full length NRS 1 nM treatment, F10: full length NRS 10 nM treatment, NO. 1: NRS N-term fragment 0.1 nM treatment, N1: the NRS N-terminal fragment 1 nM treatment, N10: the NRS N-terminal fragment 10 nM treatment, C0.1: the NRS catalytic domain peptide 0.1 nM treatment, C1: the NRS catalytic domain peptide 1 nM treatment, and C10: NRS catalytic domain peptide 10 nM treatment).

Figure 7:
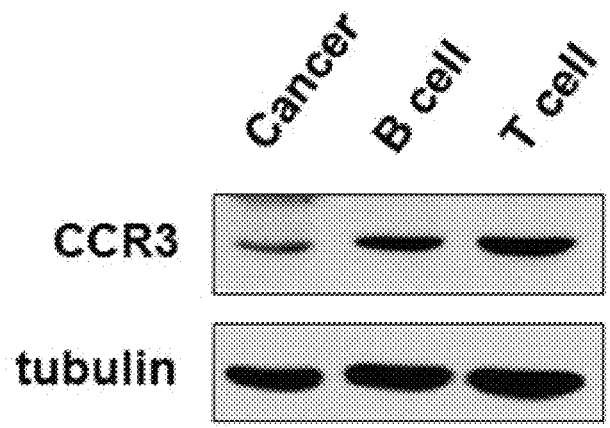

FIG. 7 shows the results of measuring the expression of CCR3 in cancer cells or lymphocytes (T cell, B cell) by Western blotting (T lymphocyte: Jurkat, B lymphocyte: Daudi, Cancer cell: H460).

Figure 8:
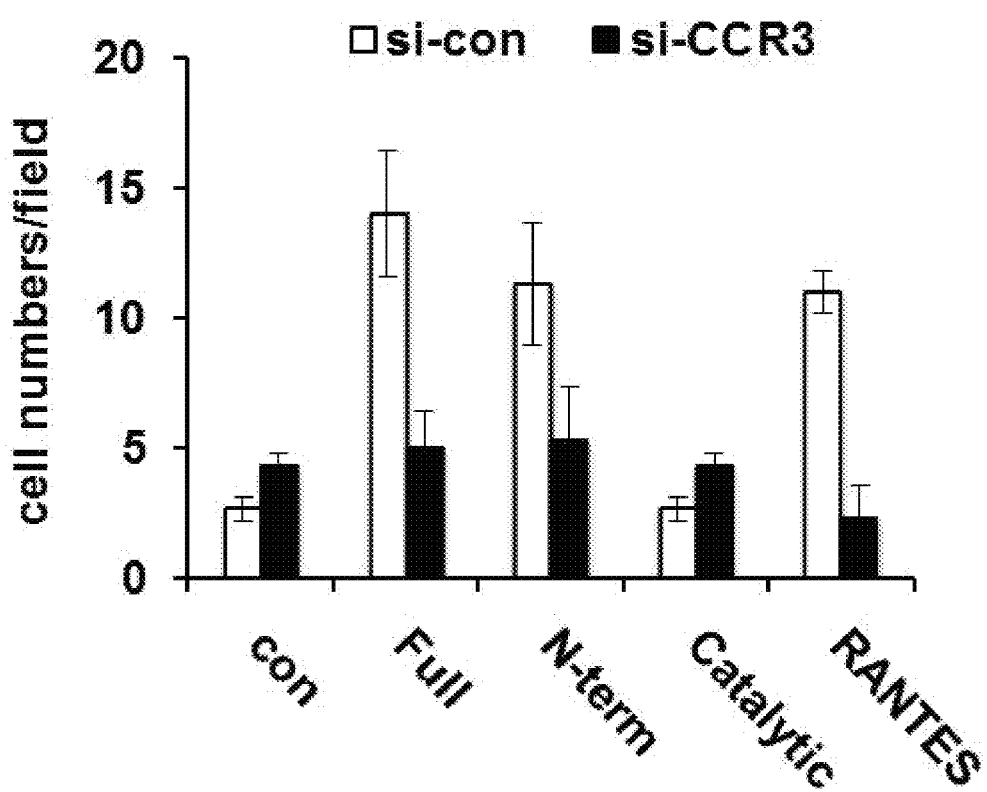

FIG. 8 shows the results of quantifying the effect of knock-down on CCR3 in lymphocyte migration. CCR3-knockdown cells using CCR3-targeting siRNA (si-CCR3) were used for cell migration assay in a transwell chamber. After treatment of full length NRS, NRS N-term fragment of the present invention, NRS catalytic domain peptide, and RANTES (positive control) in the lower chamber, the cells migrated from the membrane of the upper chamber were counted under a microscope.

Figure 9:
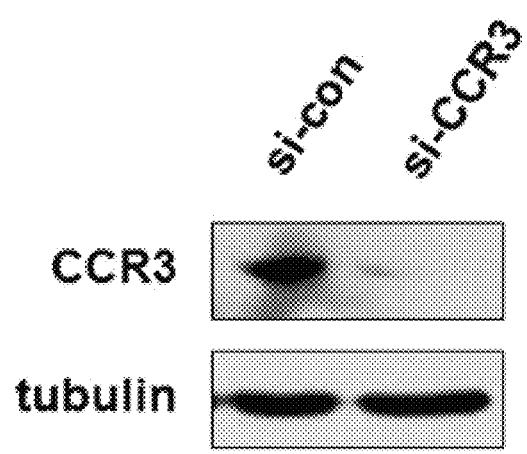

FIG. 9 shows the result of confirming the knock-down of CCR3 using CCR3-targeting siRNA (si-CCR3) by Western blotting.

MODE FOR CARRYING OUT INVENTION

Hereinafter, the present invention will be described in detail.

However, the following examples are illustrative of the present invention, and the present invention is not limited to the following examples.

Example 1

Preparation of Recombinant NRS N-Terminal Extension M1-977 Protein

1) Fusion Protein Construction of MBP-NRS N-Terminal Extension

The present inventors constructed recombinant proteins using the pET-28a vector (Novagen) to overexpress the NRS N-terminal extension protein and to obtain high solubility proteins. Maltose binding protein (MBP)-Tobacco etch virus (TEV) protease cleavage site-NRS N-terminal extension was fused to the pET-28a vector. The following is protein sequence information fused with maltose binding protein.

MGSSHHHHHHSKIEEGKLVIWINGDKGYNGLAEVGKKFEKDTGIKVTVEH

PDKLEEKFPQVAATGDGPDIIFWAHDRFGGYAQSGLLAEITPDKAFQDKL

YPFTWDAVRYNGKLIAYPIAVEALSLIYNKDLLPNPPKTWEEIPALDKEL

KAKGKSALMFNLQEPYFTWPLIAADGGYAFKYENGKYDIKDVGVDNAGAK

AGLTFLVDLIKNKHMNADTDYSIAEAAFNKGETAMTINGPWAWSNIDTSK

VNYGVTVLPTFKGQPSKPFVGVLSAGINAASPNKELAKEFLENYLLTDEG

LEAVNKDKPLGAVALKSYEEELAKDPRIAATMENAQKGEIMPNIPQMSAF

WYAVRTAVINAASGRQTVDEALKDAQTNSSSENLYFQGHMVLAELYVSDR

EGSDATGDGTKEKPFKTGLKALMTVGKEPFPTIYVDSQKENERWNVISKS

QLKNIKKMWHREQMKS*

After cleavage with TEV protease, the NRS N-term protein was obtained with the GH amino acid remaining at the N terminus of NRS sequence 1-77. Nde1 and Xho1 restriction sites were used to insert the human NRS sequence into the vector.

2) *E. coli* Culture and Protein Overexpression Comprising Recombinant MBP-NRS N-Terminal Extension Protein

*Escherichia coli* Rosetta2 (DE3) (Novagen) was transformed by heat-shock protocol using a vector constructed to express the recombinant protein MBP-NRS N-terminal extension, and colonies with kanamycin resistance were selected by culturing in LB medium containing kanamycin (+30 mg/L). The selected colonies were used to inoculate the seed culture for mass culture in LB liquid medium containing kanamycin (+30 mg/L) for 16 hours at 37° C. A part of the seed culture was inoculated into the main cultured LB medium (2%) containing kanamycin and the expression of the recombinant protein was induced by 0.5 mM IPTG (Isopropyl-beta-D-thiogalactopyranoside) when the 00600 reached 0.5 at 37° C. The expression-induced cultures were incubated for about 8 hours at 37° C. and then centrifuged at 6000 g for 10 minutes at 4° C. to recover the bacterial precipitates.

3) Protein Purification of Recombinant NRS N-Terminal Extension

The recovered cell precipitate was suspended in a crushing solution [35 mM Imidazole, 500 mM NaCl, 20 mM Tris-HCl (pH 7.5)/10 mL of crushed solution per 1 g of cells]. After adding 100 mM PMSF (Phenylmethylsulfonyl Fluoride/100 mM PMSF 100 µl per 1 g cell) to the suspension, the suspension was disrupted using an ultrasonic disintegrator (SONICS). After crushing, the supernatant was centrifuged to be separated at 35000 g for 60 minutes at 4° C. The supernatant was filtered using a 0.45-μm nitrocellulose membrane filter (Sartorius) and loaded onto a HiTrap Chelating HP (GE Healthcare) column packed with nickel using Pump P-1 (GE Healthcare). The loaded column was connected to FPLC (GE Healthcare), and then the recombinant proteins were firstly separated and purified by a 50% gradient elution method using an elution solution (1 M Imidazole, 500 mM NaCl, 20 mM Tris-HCl, pH 7.5). The purified recombinant protein was replaced with a TEV Protease treatment solution (200 mM NaCl, 20 mM Tris-HCl, pH 7.5) using HiPrep 26/10 Desalting (GE Healthcare) column and 1 mg of TEV protease was treated at 4° C. for 20 hours to separate MBP and NRS N-terminal extension. Thereafter, it was loaded again on a HiTrap Chelating HP (GE Healthcare) column filled with nickel using Pump P-1 (GE Healthcare). The loaded column was connected to FPLC (GE Healthcare), and then the proteins were secondly separated and purified by a 50% gradient elution method using an elution solution (1 M Imidazole, 500 mM NaCl, 20 mM Tris-HCl, pH 7.5). Secondarily separated recombinant proteins were used to separate and purify tertiary protein using size exclusion chromatography [HiLoad16/600 Superdex75 (GE Healthcare), and PBS buffer], and thus the final NRS N-terminal extension domain (SEC) ID NO: 1) was obtained.

Comparative Example 1

Production of Full-Length NRS Protein

A full-length NRS (SEQ ID NO: 2) expression gene was inserted between the Nde1 site and the Xho1 site of the pET-28a (NOVAGEN) vector. The constructed recombinant vector was used to transform E. coli strain 041 (DE3). The transformed cells were cultured in LB medium containing kanamycin at 37° C. using a shaking incubator. When $OD_{600nm}$ reached 0.5, IPTG (Isopropyl-D-1-thiogalactopyranoside) was added to the cultured cells to induce the expression of full-length NRS. After IPTG treatment, cell cultures were incubated at 37° C. for 8 hours in a shaking incubator. The cultured E. coli cells were harvested by centrifugation at 6,000 g for 10 minutes. The collected cells were resuspended in a buffer containing 500 mM NaCl, 20 mM Tris-HCl, and 35 mM imidazole (pH 7.5), and the cells were lysed with an ultrasonic processor.

Purification and obtaining of the target protein in the cell lysate was carried out as follows. First, the dissolved cell sample was centrifuged at 35,000 g for 1 hour and filtered through a 0.45 μm syringe filter device (Sartorius). The obtained samples were loaded on a Ni (H) ion-charged HiTrap 5 ml chelating HP column (GE HEALTHCARE) using a peristaltic pump. The loaded sample was eluted into a buffer containing 500 mM NaCl, 20 mM Tris-HCl, and 1 M imidazole (pH 7.5) using a 50% gradient elution method. Fractions containing full length NRS were desalted in a buffer containing 50 mM NaCl, 20 mM Tris-HCl (pH 7.5) using a HiPrep desalting 26/10 (GE HEALTHCARE) column. The desalted sample was loaded on a HiTrap 5 ml Q HP (GE Healthcare) column and eluted in a buffer solution containing 1 M NaCl, 20 mM Tris-HCl (pH 7.5) using a 50% gradient elution method. The obtained fractions were loaded on a HiLoad 16/600 Superdex 200 pg (GE HEALTHCARE) column, eluted in PBS buffer (137 mM NaCl, 2.7 mM KCl, 4.3 mM $Na_2HPO_4$, 1.4 mM $KH_2PO_4$, pH 7.4), and then a protein sample of full-length NRS (SEQ ID NO: 2) was finally obtained. And the protein samples were mixed with 10% glycerol, Protein purity was confirmed by 20 electrophoresis in each step of purification.

Comparative Example 2

High Purity Preparation of the NRS Catalytic Domain

The NRS catalytic domain (98-548) gene was inserted between the Nde1 site and the Xho1 site of the pET-28a (NOVAGEN) vector. Solu-BL21, an E. coli strain, was transformed using the recombinant vector. The transformed cells were cultured in LB medium containing kanamycin at 37° C. using a shaking incubator. When $OD_{600nm}$ reached 0.5, IPTG (Isopropyl-D-1-thiogalactopyranoside) was added to the cultured cells to induce the expression of the NRS catalytic domain fragment. After IPTG treatment, cell cultures were incubated at 37° C. for 8 hours in a shaking incubator. Cultured E. coli cells were harvested by centrifugation at 6,000 g for 10 min. The collected cells were resuspended in a buffer containing 500 mM NaCl, 20 mM Tris-HCl, and 35 mM imidazole (pH 7.5), and the cells were lysed with an ultrasonic processor. The NRS catalytic domain (98-548) fragment from the cell lysate was obtained in the same manner as in the protein purification process in Comparative Example 1 described above.

Example 2

Identification of Cytokine Activity of the Recombinant NRS-Terminal Extension M1-S77 Protein Preparation of Experiment 1. Cell Culture and Sample A549, H460, J774A.1, WI-26, Daudi, and Jurkat cells were cultured in RPMI1640 medium (Hyclone) containing 10% fetal bovine serum and antibiotics (100 UI penicillin and 100 mg/ml streptomycin). DMEM media containing 10% fetal bovine serum and antibiotics (100 UI penicillin and 100 mg/ml streptomycin) were used for the culture of RAW 2647. The anti-CCR3 antibody (Millipore), the anti-tubulin antibody (Sigma) and the anti-NRS antibody (Abcam) were used.

2. Cell Migration Assay

Cell migration was measured using a Boyden Transwell plate (5 mm pore size, 24 well, Corning). First, the membrane was pre-coated with 50 μg/ml fibronectin (BD Biosciences) and the cells were placed in the upper chamber. The NRS N-term extension domain and RANTES were added to the lower chamber as inducers and positive controls, respectively. After 4 hours of incubation, the membrane was washed twice with PBS, and cells were fixed with PBS containing 70% methyl alcohol. The membrane was then stained with hematoxylin (Sigma-Aldrich), The upper non-migrating cells were removed by a swab. The membrane was cut and mounted on a slide glass. The transferred cells were observed and counted under a microscope using a 20× objective lens.

3. Secretion Essay

Cells were cultured at 70% confluency after being spread. The cells were washed twice with PBS and then cultured under various conditions as follows; (i) Incubation in serum-free medium for 6 hours, and (ii) Incubation for 4 hours with TNF-α, IFN-γ and TGH-β added at a concentration of 10 ng/ml.

After the culture medium was collected, centrifugation was sequentially performed at 1,000 g for 10 minutes and 10,000 g for 20 minutes in order to remove cells and debris. To precipitate the protein, trichloroacetic acid (TCA, Sigma) was added to a final concentration of 10%. After 12 hours incubation, the secreted proteins were pelleted by centrifugation at 20,000 g. The precipitated proteins were suspended in 100 mM HEPES (pH 8.0) and then used for separation by SDS-PAGE and Western blotting.

4. Western Blot

Cells on ice were lysed with M-PER (Pierce). After cell debris was removed by centrifugation, protein concentration was measured by Bradford solution (Bio-Rad) according to the manufacturers method. The proteins were then separated by SDS-PAGE, transferred to a PVDF membrane, and then subjected to Western blotting using antibodies specific for each target protein. The primary anti-CCR3 antibody (Millipore), the anti-tubulin antibody (Sigma), and the anti-NRS antibody (Abcam) were used. HRP-conjugated goat anti-rabbit IgG was purchased from Thermo for NRS as a secondary antibody, and HRS conjugated goat anti-mouse IgG was purchased from Thermo for tubulin.

Experimental Results

1. Th1 Cytokines Induce the Secretion of NRS from Macrophages.

Figure 2:
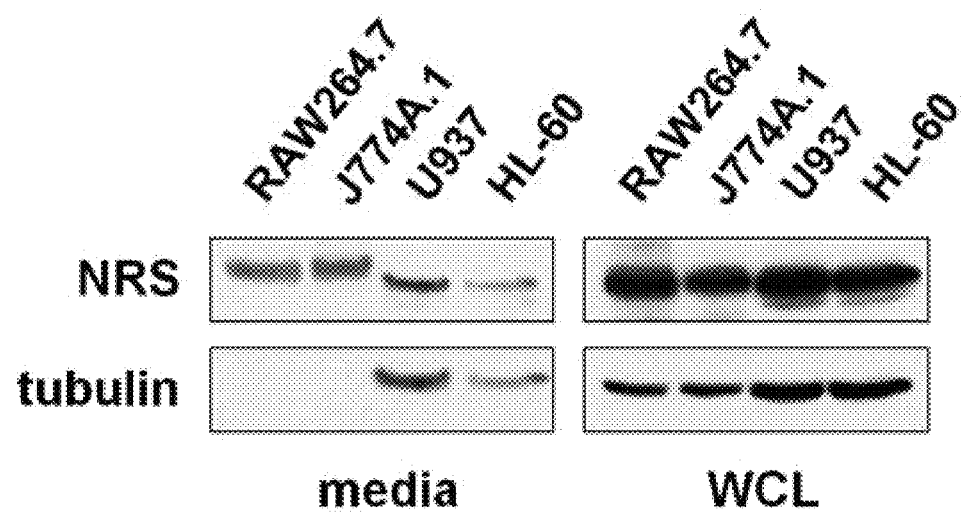

Autoantibodies to NRS are detected in patients with autoimmune and interstitial lung disease (ILD). Several cell lines were tested to find cells capable of secreting NRS. Nine different cell lines (A549, H460, WI-26, Daudi, Jurkat, RAW264.7, J774A.1, U937 and HL-60) were cultured in serum-free medium for 6 hours, and proteins secreted in the medium were precipitated by TCA. The precipitated proteins were separated by SDS PAGE and the presence of NRS was measured by Western blotting using anti-NRS antibody. Of the nine cell lines, NRS was only detected in the culture media of RAW 264.7 and J774A.1 (see FIGS. 1 and 2) cells which are macrophage cells. Under the same conditions as above, tubulin release was not observed in the medium. As a result, it was confirmed that the NRS contained in the medium after culture was not due to cell lysis. These results suggest that NRS is secreted from macrophages. Several different signaling molecules such as TNF-α, IFN-γ and TGF-β were treated in RAW 264.7 cells to determine if NRS secretion could be induced by other stimulus sources. TNF-a and IFN-y are known to affect Th1 differentiation. In contrast, TGF-β is known to modulate Th2 differentiation. Among these, it was observed that TNF-α and IFN-γ induced NRS secretion at 4 hours after treatment (see FIG. 3). Based on these results, it was verified that NRS is secreted from macrophages, especially under Th1 differentiation conditions.

2. The N-Term Extension Domain of NRS Induces Cell Migration of Lymphocytes.

Cell migration was monitored using a transwell chamber. The catalytic domain of NRS did not affect lymphocyte migration, whereas full length NRS and NRS N-term extension domain induced lymphocyte migration (see FIGS. 4 to 6). These results suggest that the N-term extension domain has the chemokine-like activity of NRS. In order to observe the chemokine-like activity of NRS in other types of cells, NRS N-term extension domain was treated on cancer cells and NRS N-term extension domain fragments did not activate cancer cell migration (FIG. 4). Since CCR3 has been shown to be a functional receptor for NRS, CCR3 expression levels were compared in cancer cells and lymphocytes, CCR3 expression was up-regulated in lymphocytes, but not in cancer cells (see FIG. 7). Since CCR3 expression was high in lymphocytes, we compared the chemokine-like activity of NRS in CCR3 knock-down lymphocytes. When CCR3 was inhibited by si-CCR3 (FIG. 9), the cell migration activity by the full length NRS or NRS N-term extension domain decreased (see FIG. 8). These results indicate that the N-term extension domain of NRS is a major part of the chemokine-like activity of NRS and that CCR3 is a receptor for the chemokine-like activity of NRS.

INDUSTRIAL APPLICABILITY

As described above, the present invention relates to a novel polypeptide having chemokine activity, and more particularly, to a polypeptide consisting of an amino acid sequence represented by SEQ ID NO: 1 and its use. Since the polypeptide of the present invention is composed of SEQ ID NO: 1 and exhibits chemokine activity through binding to CCR3, it can be used for various purposes such as immuno-regulation, detection, diagnosis and treatment of CCR3-mediated diseases or pathologies, and the development of a therapeutic agent therefor, which is highly likely to be used industrially.

What is claimed is:

1. A polypeptide having a chemokine activity mediated by binding to C-C chemokine receptor type 3 (CCR3) consisting of the amino acid sequence of SEQ ID NO: 1.

2. A therapeutic composition comprising the polypeptide of claim 1 and a pharmaceutically acceptable carrier.

3. A polypeptide having a chemokine activity mediated by binding to C-C chemokine receptor type 3 (CCR3) comprising the amino acid sequence of SEQ ID NO: 1 and two additional amino acids at its N-terminus, wherein the polypeptide comprises 77 to 100 amino acids.

4. The polypeptide of claim 3, wherein the two amino acids are glycine and histidine.

5. A therapeutic composition comprising the polypeptide of claim 3 and a pharmaceutically acceptable carrier.

6. A method for screening an agent for preventing or treating a CCR3-mediated disease, the method comprising (a) determining whether an agent inhibits the chemokine activity of the polypeptide of claim 1 or a full-length Asparaginyl-tRNA (NRS) consisting of the amino acid sequence of SEQ ID NO: 2 by contacting the agent with the polypeptide consisting of the amino acid sequence of SEQ ID NO: 1 or the full-length Asparaginyl-tRNA (NRS) consisting of the amino acid sequence of SEQ ID NO: 2;

(b) selecting an agent inhibiting chemokine activity in step (a); and (c) determining whether CCR3 activity is inhibited by treating cells expressing CCR3 with the agent selected in step (b).

7. A method for detecting a choroidal neovascularization in a subject, the method comprising administering an effective amount of a composition comprising the polypeptide of claim 1 to the subject and detecting binding of the polypeptide of claim 1 to CCR3 expressed in choroidal neovascular endothelial cells of the subject.

8. The method of claim 7, wherein the polypeptide in the composition is labeled with a radioisotope, a chromophore, a luminescent material, a fluorescer, a magnetic resonance imaging material, super paramagnetic particles, or ultrasuper paramagnetic particles.

9. A method for diagnosing a CCR3-mediated disease in a subject, the method comprising administering an effective amount of a composition comprising the polypeptide of claim 1 to the subject and detecting binding of the polypeptide of claim 1 to CCR3 in the subject.

10. The method of claim 9, wherein the CCR3-mediated disease is asthma, allergic rhinitis, hypersensitive lung disease, hypersensitivity pneumonia, eosinophilic pneumonia, respiratory allergic disease, or eczema.

11. The method of claim 9, wherein the CCR3-mediated disease is psoriasis, dermatitis or inflammatory skin disease.

12. The method of claim 9, wherein the CCR3-mediated disease is inflammatory bowel disease.

13. The method of claim 9, wherein the CCR3-mediated disease is a kidney cancer or a prostate cancer.

14. A method for a CCR3-mediated disease-specific drug delivery to a subject with a CCR3-mediated disease, the method comprising administering an effective amount of a composition comprising the polypeptide of claim 1 to the subject to treat the subject's CCR3-mediated disease.

15. The method of claim 14, wherein the CCR3-mediated disease is asthma, allergic rhinitis, hypersensitive lung disease, hypersensitivity pneumonia, eosinophilic pneumonia, respiratory allergic disease, or eczema.

16. The method of claim 14, wherein the CCR3-mediated disease is psoriasis, dermatitis or inflammatory skin disease.

17. The method of claim 14, wherein the CCR3-mediated disease is inflammatory bowel disease.

18. The method of claim 14, wherein the CCR3-mediated disease is a kidney cancer or a prostate cancer.

* * * * *

SEQUENCE LISTING

```
<160> NUMBER OF SEQ ID NOS: 3

<210> SEQ ID NO 1
<211> LENGTH: 77
<212> TYPE: PRT
<213> ORGANISM: Artificial Sequence
<220> FEATURE:
<223> OTHER INFORMATION: NRS N-terminal extension fragment

<400> SEQUENCE: 1

Met Val Leu Ala Glu Leu Tyr Val Ser Asp Arg Glu Gly Ser Asp Ala
1               5                   10                  15

Thr Gly Asp Gly Thr Lys Glu Lys Pro Phe Lys Thr Gly Leu Lys Ala
            20                  25                  30

Leu Met Thr Val Gly Lys Glu Pro Phe Pro Thr Ile Tyr Val Asp Ser
        35                  40                  45

Gln Lys Glu Asn Glu Arg Trp Asn Val Ile Ser Lys Ser Gln Leu Lys
    50                  55                  60
```

Asn Ile Lys Lys Met Trp His Arg Glu Gln Met Lys Ser
65                  70                  75

<210> SEQ ID NO 2
<211> LENGTH: 548
<212> TYPE: PRT
<213> ORGANISM: Artificial Sequence
<220> FEATURE:
<223> OTHER INFORMATION: Human NRS

<400> SEQUENCE: 2

Met Val Leu Ala Glu Leu Tyr Val Ser Asp Arg Glu Gly Ser Asp Ala
1               5                   10                  15

Thr Gly Asp Gly Thr Lys Glu Lys Pro Phe Lys Thr Gly Leu Lys Ala
            20                  25                  30

Leu Met Thr Val Gly Lys Glu Pro Phe Pro Thr Ile Tyr Val Asp Ser
        35                  40                  45

Gln Lys Glu Asn Glu Arg Trp Asn Val Ile Ser Lys Ser Gln Leu Lys
    50                  55                  60

Asn Ile Lys Lys Met Trp His Arg Glu Gln Met Lys Ser Glu Ser Arg
65                  70                  75                  80

Glu Lys Lys Glu Ala Glu Asp Ser Leu Arg Arg Glu Lys Asn Leu Glu
                85                  90                  95

Glu Ala Lys Lys Ile Thr Ile Lys Asn Asp Pro Ser Leu Pro Glu Pro
            100                 105                 110

Lys Cys Val Lys Ile Gly Ala Leu Glu Gly Tyr Arg Gly Gln Arg Val
        115                 120                 125

Lys Val Phe Gly Trp Val His Arg Leu Arg Arg Gln Gly Lys Asn Leu
    130                 135                 140

Met Phe Leu Val Leu Arg Asp Gly Thr Gly Tyr Leu Gln Cys Val Leu
145                 150                 155                 160

Ala Asp Glu Leu Cys Gln Cys Tyr Asn Gly Val Leu Leu Ser Thr Glu
                165                 170                 175

Ser Ser Val Ala Val Tyr Gly Met Leu Asn Leu Thr Pro Lys Gly Lys
            180                 185                 190

Gln Ala Pro Gly Gly His Glu Leu Ser Cys Asp Phe Trp Glu Leu Ile
        195                 200                 205

Gly Leu Ala Pro Ala Gly Gly Ala Asp Asn Leu Ile Asn Glu Glu Ser
    210                 215                 220

Asp Val Asp Val Gln Leu Asn Asn Arg His Met Met Ile Arg Gly Glu
225                 230                 235                 240

Asn Met Ser Lys Ile Leu Lys Ala Arg Ser Met Val Thr Arg Cys Phe
                245                 250                 255

Arg Asp His Phe Phe Asp Arg Gly Tyr Tyr Glu Val Thr Pro Pro Thr
            260                 265                 270

Leu Val Gln Thr Gln Val Glu Gly Gly Ala Thr Leu Phe Lys Leu Asp
        275                 280                 285

Tyr Phe Gly Glu Glu Ala Phe Leu Thr Gln Ser Ser Gln Leu Tyr Leu
    290                 295                 300

Glu Thr Cys Leu Pro Ala Leu Gly Asp Val Phe Cys Ile Ala Gln Ser
305                 310                 315                 320

Tyr Arg Ala Glu Gln Ser Arg Thr Arg Arg His Leu Ala Glu Tyr Thr
                325                 330                 335

His Val Glu Ala Glu Cys Pro Phe Leu Thr Phe Asp Asp Leu Leu Asn
            340                 345                 350

```
Arg Leu Glu Asp Leu Val Cys Asp Val Val Asp Arg Ile Leu Lys Ser
            355                 360                 365

Pro Ala Gly Ser Ile Val His Glu Leu Asn Pro Asn Phe Gln Pro Pro
    370                 375                 380

Lys Arg Pro Phe Lys Arg Met Asn Tyr Ser Asp Ala Ile Val Trp Leu
385                 390                 395                 400

Lys Glu His Asp Val Lys Lys Glu Asp Gly Thr Phe Tyr Glu Phe Gly
                405                 410                 415

Glu Asp Ile Pro Glu Ala Pro Glu Arg Leu Met Thr Asp Thr Ile Asn
            420                 425                 430

Glu Pro Ile Leu Leu Cys Arg Phe Pro Val Glu Ile Lys Ser Phe Tyr
            435                 440                 445

Met Gln Arg Cys Pro Glu Asp Ser Arg Leu Thr Glu Ser Val Asp Val
    450                 455                 460

Leu Met Pro Asn Val Gly Glu Ile Val Gly Gly Ser Met Arg Ile Phe
465                 470                 475                 480

Asp Ser Glu Glu Ile Leu Ala Gly Tyr Lys Arg Glu Gly Ile Asp Pro
                485                 490                 495

Thr Pro Tyr Tyr Trp Tyr Thr Asp Gln Arg Lys Tyr Gly Thr Cys Pro
            500                 505                 510

His Gly Gly Tyr Gly Leu Gly Leu Glu Arg Phe Leu Thr Trp Ile Leu
            515                 520                 525

Asn Arg Tyr His Ile Arg Asp Val Cys Leu Tyr Pro Arg Phe Val Gln
            530                 535                 540

Arg Cys Thr Pro
545

<210> SEQ ID NO 3
<211> LENGTH: 231
<212> TYPE: DNA
<213> ORGANISM: Artificial Sequence
<220> FEATURE:
<223> OTHER INFORMATION: Polynucleotide encoding human NRS N-terminal
      extension fragment

<400> SEQUENCE: 3
atggtgcttg cagagctgta cgtctctgac cgagagggaa gcgatgccac gggagatgga      60
accaaggaga aaccatttaa aacaggtcta aaggctttga tgacagtagg gaaagaacca     120
tttcctacca tttacgtaga ttcacaaaaa gaaaatgaga ggtggaatgt tatttctaaa     180
tcacagttga agaacattaa aaagatgtgg catagggaac aaatgaagag t              231
```